(12) United States Patent
Suzuki et al.

(10) Patent No.: US 8,067,631 B2
(45) Date of Patent: Nov. 29, 2011

(54) METHOD OF RAPID METHYLATION OF ALKENE COMPOUND AND KIT FOR PET TRACER PREPARATION USING THE SAME

(75) Inventors: Masaaki Suzuki, Gifu (JP); Takamitsu Hosoya, Yokohoma (JP)

(73) Assignee: Gifu University, Gifu-shi, Gifu (JP)

( * ) Notice: Subject to any disclaimer, the term of this patent is extended or adjusted under 35 U.S.C. 154(b) by 689 days.

(21) Appl. No.: 12/090,642

(22) PCT Filed: Oct. 6, 2006

(86) PCT No.: PCT/JP2006/320104
§ 371 (c)(1),
(2), (4) Date: Apr. 17, 2008

(87) PCT Pub. No.: WO2007/046258
PCT Pub. Date: Apr. 26, 2007

(65) Prior Publication Data
US 2009/0238759 A1    Sep. 24, 2009

(30) Foreign Application Priority Data
Oct. 21, 2005    (JP) ................................ 2005-306670

(51) Int. Cl.
C07C 69/74 (2006.01)
C07C 45/00 (2006.01)
C07C 35/00 (2006.01)
C07C 11/02 (2006.01)

(52) U.S. Cl. ......... 560/128; 568/364; 568/875; 585/601

(58) Field of Classification Search ........................ None
See application file for complete search history.

(56) References Cited

OTHER PUBLICATIONS

Suzuki et al., {Rapid Methylation for the Synthesis of a 11C-Labeled Tolylisocarbacyclin Imaging the IP2 Receptor in a Living Human Brain, Tetrahedron, vol. 56, Issue 42, Oct. 13, 2000, pp. 8263-8273}.*
Hosoya et al., {Rapid methylation of terminal acetylenes by the Stille coupling of methyl iodide with alkynyltributylstannanes: a general protocol potentially useful for the synthesis of short-lived 11CH3-labeled PET tracers with a 1-propynyl group, Org. Biomol. Chem., 2004, 2, 24-27}.*
Hosoya et al., {Rapid methylation on carbon frameworks useful for the synthesis of 11CH3-incorporated PET tracers: Pd(0)-mediated rapid coupling of methyl iodide with an alkenyltributylstannane leading to a 1-methylalkene, Org. Biomol. Chem., 2006, 4, 410-415}.*
Tang et al., {Ligands for Palladium-Catalyzed Cross-Couplings of Alkyl Halides: Use of an Alkyldiaminophosphane Expands the Scope of the Stille Reaction, Chem. Int. ed. 2003, 42, 5079-5082}.*
Menzel et al., {Room-Temperature Stille Cross-Couplings of Alkenyltin Reagents and Functionalized Alkyl Bromides that Possess Hydrogens, J. Am. Chem. Soc. 2003, 125, 3718-3719}.*
White et al, Basic Energy Sciences Advisory Committee Subpanel Workshop Report, Opportunities for Catalysis in the 21st Century, 2002, pp. 1-47.*
Suzuki et al., Rapid Coupling of Methyl Iodide with Aryltributylstannanes Mediated by Palladium(o) Complexes: A General protocol for the Synthesis of 11CH3-Labeled PET Tracers, Chemistry—A European Journal, Wiley—V C H Verlag GmbH & Co. KGAA, Weinheim, DE, vol. 3, No. 12, Jan. 1, 1997, pp. 2039-2042.
Bjorkman, M., "Synthesis of a 11C-Labelled Prostaglandin F2a Analogue Using an Improved Method for Stille Reactions with [11C]Methyl Iodide," Journal of Labelled Compounds and Radiopharmaceuticals, vol. 43, 2000, pp. 1327-1344.
Madsen, J., et al.; Synthesis and Biological Evaluation of Novel Carbon—11-Labelled Analogues of Citalopram as Potential Radioligands for the Serotonin Transporter, Bioorganic and Medicinal Chemistry, vol. 11, 2003, pp. 3447-3456.
Suzuki, Masaaki et al., "Rapid Coupling of Methyl Iodide with Aryltributylstannanes Mediated by Palladium(0) Complexes: A General Protocol for the Synthesis of 11CH3-Labeled PET Tracers," Chem. Eur. J., 3(12), 1997, pp. 2039-2042.
Suzuki, Masaaki et al., "Rapid Methylation for the Synthesis of a 11CH3-Labeled Tolylisocarbacyclin Imaging the IP2 Receptor in a Living Human Brain," Tetrahedron, 56, 2000, pp. 8263-8273.
Mee, Simon P. H. et al., "Stille Coupling Made Easier-The Synergic Effect of Copper Salts and the Fluoride Ion," Angew.Chem.Int.Ed., 43, 2004, pp. 1132-1136.
Mee, Simon P.H. et al., "Significant Enhancement of the Stille Reaction with a New Combination of Reagents-Copper Iodide with Cesium Fluoride," Chem. Eur. J., 11(11), May 20, 2005, pp. 3294-3308.
Fuwa, Haruhiko et al., "Total Synthesis of (−)-Gamblerol," J.Am. Chem.Soc., 124,2002, pp. 14983-14992.
Menzel, K. et al., Room-Temperature Stille Cross-Couplings of Alkenyltin Reagents and Functionalized Alkyl Bromides that Possess β Hydrogens; J.Am.Chem.Soc., 125,2003, pp. 3718-3719.
Tang, Haifeng et al., "Ligands for Palladium-Catalyzed Cross-Couplings of Alkyl Halides: Use of an Alkyldiaminophosphane Expands the Scope of The Stille Reaction," Int. Ed. Engl., 2003, 42, 5079-5082.

* cited by examiner

*Primary Examiner* — Paul A Zucker
(74) *Attorney, Agent, or Firm* — Quarles & Brady LLP; Gavin J. Milczarek-Desai

(57) ABSTRACT

To provide a method of rapid methylation of alkenes, which is applicable to the preparation of a PET tracer and which enables alkenes to be methylated through cross coupling between $SP^2$ (alkenyl) and $SP^3$ (alkyl) carbon atoms rapidly and in a high yield. Methyl iodide and an alkenyltrialkylstannane are subjected to cross coupling in an aprotic polar solvent in the presence of a palladium complex having a valence of 0, a phosphine ligand, a cuprous halide, and a carbonate and/or alkali metal fluoride.

8 Claims, No Drawings

METHOD OF RAPID METHYLATION OF ALKENE COMPOUND AND KIT FOR PET TRACER PREPARATION USING THE SAME

TECHNICAL FIELD

The present invention relates to a method of rapid methylation of alkenes, in which methyl iodide and alkenyltrialkylstannane are subjected to cross coupling in a short time so as to form methyl alkene, and a kit for preparing a PET tracer using the same. The present invention can be suitably used as a method for manufacturing a tracer used in positron emission tomography (hereinafter, referred to as "PET").

BACKGROUND ART

In a PET method, a labeled compound labeled with short-lived radionuclide that emits positron is administered into a living body, γ rays generated by this labeled compound (hereinafter, referred to as "tracer") are measured by using a PET camera (a detector including a gamma-ray scintillator and a photomultiplier), and the distribution thereof in the body is imaged by using a computer. This PET method is used in identification of a site of a tumor such as a cancer cell as an examination of nuclear medicine; a diagnosis of Alzheimer disease, brain infarction, and the like; a diagnosis of a mental disorder such as depression; an evaluation of treatment; and an evaluation of pharmacokinetics and drug efficacy.

A PET method uses a tracer labeled with a short-lived radionuclide such as $^{11}C$, $^{18}F$, and the like. Among them, a $^{11}C$-labeled tracer has many advantages as mentioned below.

(1) Since a $^{11}C$-labeled tracer uses a carbon atom existing in all organic compounds, it is applicable in an extremely wide range.

(2) A method for preparing compounds such as $^{11}CH3I$, $^{11}CO$, $^{11}CO2$ serving as a precursor for synthesizing a $^{11}C$-labeled tracer is well established. Therefore, purified precursors can be stably obtained.

(3) Since a $^{11}C$-containing tracer has a short half-life (20.3 min), it is possible to carry out a large number of trials and clinical tests for basic studies in a day. Furthermore, it is not necessary to pay a particular attention to processing of radio-labeled byproducts generated after a synthesis reaction, and the like.

Therefore, it can be said that the $^{11}C$-labeled tracer is the most excellent tracer used in the PET method. However, since the half-life of $^{11}C$ is such an extremely short time as 20 minutes, it is necessary to carry out purification and administration of the product within 40 minutes after starting the reaction. Therefore, a synthesizing reaction of the tracer has to be completed for about 5 to 10 minutes. A method for carrying out a rapid reaction in a high yield has not been established, which has been an obstacle in using a $^{11}C$-labeled tracer in the PET method.

By the way, a method for synthesizing a PET tracer using $^{11}C$ as a radionuclide includes a method of binding a $^{11}C$-labeled methyl group to a heteroatom such as O, C, N, and the like, and a method of binding a $^{11}C$-labeled methyl group to carbon of the carbon skeleton. The tracers obtained by binding a $^{11}C$-labeled methyl group to a heteroatom such as O, C, N, and the like, are often changed into other compounds rapidly by the metabolism in the body. Therefore, when such tracers are clinically used, the tracers may be changed before they reach the target organ, thus making it impossible to conduct a diagnosis and to provide a treatment accurately. Furthermore, since a compound after methylation shows an utterly different bioactivity from that of a compound before methylation, it is not suitable as a means for searching a candidate for drug discovery. On the contrary, the tracer obtained by binding $^{11}C$ methyl to carbon of the carbon skeleton has the following advantages: (1) Since a methyl group is a three-dimensionally smallest and non-polar functional group, the effect of the methyl group on the parent compound after it is introduced is minimum; and (2) Since a C-methylated product shows higher stability with respect to the metabolism as compared with an O-methylated product or a N-methylated product, the resultant image has higher reliability and an appropriate diagnosis of disease can be conducted.

Under such circumstances, the present inventors have developed a rapid methylation method in which methyl iodide and an organic tin compound are subjected to a Stille-coupling reaction, and received much attention (non-patent document 1). This method has enabled a cross coupling between $SP^2$ and $SP^3$ carbons atoms, which has been considered to be conventionally difficult in the Stille-coupling reaction. For example, when methyl iodide, an excess tributyl (phenyl)stannane, tri-o-tolylphosphine and unsaturated palladium are reacted in a DMF solvent in the presence of copper salt and potassium carbonate at 60° C. for 5 minutes, methylation proceeds in a yield of 90% or more. This method has been demonstrated to be useful. For example, this method has been actually applied to a prostaglandin derivative tracer and succeeded in imaging a prostaglandin receptor in the human brain.

Besides, the Stille-coupling reaction relating to the present invention has been described in the below mentioned documents (non-patent documents 2 to 4).

[Non-patent document 1] M. Suzuki, H. Doi, M. Bjorkman, Y. Anderson, B. Langstrom, Y. Watanabe and R. Noyori, Chem. Eur. J., 1997, 3(12), 2039-2042

[Non-patent document 2] K. Menzel and G. C. Fu, J. Am. Chem. Soc., 2003, 125, 3718-3719

[Non-patent document 3] H. Tang, K. Menzel and G. C. Fu, Angew, Int. Ed. Engl., 2003, 42, 5079-5082

[Non-patent document 4] J. Baldwin et al, Angew. Chem. Int. Ed., 2004, 43, 1132-1136

DISCLOSURE OF THE INVENTION

Problems to be Solved by the Invention

In the Stille-coupling reaction developed by the present inventors and described in the above-mentioned non-patent document 1, when a substituent bonded to tin is an aryl group or an alkynyl group, methylation can be carried out rapidly and in a high yield. However, when a substituent bonded to tin is an alkenyl group, a reaction for methylation thereof has not been known to date, and a rapid reaction of this type has been strongly demanded. Methyl alkenes obtained by subjecting a tin compound to which an alkenyl group is bonded and methyl iodide to a Stille-coupling reaction are frequently found as an organic compound such as isoprenoid, for example, retinoid, vitamin K, and squalene, playing an important role in the living body. Therefore, if a tin compound to which an alkenyl group is bonded and $^{11}C$-labeled methyl iodide are subjected to the Stille-coupling reaction so as to form $^{11}C$-labeled methyl alkene and if the $^{11}C$-labeled methyl alkene can be used as a PET tracer, it is expected that the application range of a PET method can be considerably widened.

The present invention has been made from the viewpoint of the above-mentioned situations. An object of the present invention is to provide a method of rapid methylation of alkenes, which enables methylation to be carried out rapidly and in a high yield by a cross coupling between $SP^2$ (alkenyl) and $SP^3$ (alkyl) carbon atoms.

Means to Solve the Problems

In order to solve the above-mentioned problems, in the Stille-coupling reaction between alkyl halide and an organic tin compound, the present inventors have applied reaction conditions described in the above-mentioned non-patent documents 2 and 4 to a cross coupling reaction between methyl iodide and alkenyltrialkylstannane. In this case, however, a target compound can be obtained only in an extremely low yield. Then, the present inventors have further investigated keenly and resulted in finding conditions capable of carrying out a Stille-coupling reaction between $SP^2$ (alkenyl) and $SP^3$ (alkyl) carbon atoms rapidly and in a high yield, and reached the present invention.

That is to say, in the first aspect of a method of rapid methylation of alkenes in accordance with the present invention, methyl iodide and alkenyltrialkylstannane are subjected to cross coupling in an aprotic polar solvent in the presence of a palladium complex having a valence of 0, a phosphine ligand, cuprous halide, carbonate and/or alkali metal fluoride.

When the method of the present invention is used, the Stille-coupling reaction between $SP^2$ (alkenyl) and $SP^3$ (alkyl) carbon atoms proceeds smoothly, and methyl alkene in which a methyl group is bonded to an alkenyl group can be obtained rapidly and in a high yield. This reaction is estimated to proceed by the following mechanism.

That is to say, firstly, a three-dimensionally bulky phosphine ligand is coordinated to a palladium complex having a valence of 0 in an unsaturated manner, thus creating an active reaction field. Then, furthermore, a palladium complex in which this phosphine ligand is coordinated and methyl iodide are reacted with each other so as to form a palladium complex having a valence of 2 in which a phosphine ligand is coordinated to $CH_3PdI$.

On the other hand, alkenyltrialkylstannane undergoes transmetallation with cuprous halide to form an alkenyl copper compound having higher nucleophilicity. Trialkylstannyl chloride generated as a by-product at this time is reacted with carbonate and alkali metal fluoride to be neutralized or precipitate (in the case of carbonate, it becomes trialkylstannyl carbonate; and in the case of alkali metal fluoride, it precipitates as trialkylstannyl fluoride) and removed from the reaction system. According to such a synergistic effect of Cu/carbonate and Cu/alkali metal fluoride, the transmetallation from Su to Cu is promoted.

Then, a divalent palladium complex in which a phosphine ligand is coordinated to $CH_3PdI$ produced as mentioned above and an alkenyl copper compound undergo a substitution reaction so as to form a complex in which a phosphine ligand is coordinated to $CH_3PdR$ (herein, R represents an alkenyl group). Furthermore, methyl alkene is formed by reductive elimination.

Furthermore, since the reaction is carried out in an aprotic polar solvent such as DMF, an aprotic polar solvent is coordinated to a vacant orbit of a palladium atom of the palladium complex generated in the middle of the reaction, so that the instability thereof is reduced and a side reaction such as decomposition can be minimized.

Therefore, according to the method of rapid methylation of alkenes of the first aspect of the present invention, alkenes can be methylated through the cross coupling between $SP^2$ (alkenyl) and $SP^3$ (alkyl) carbon atoms rapidly and in a high yield.

In the second aspect of the present invention, the carbonate is potassium carbonate or cesium carbonate. By appropriately selecting potassium carbonate or cesium carbonate depending upon the kinds of alkenyltrialkylstannanes serving as a substrate, it is possible to obtain an intended methyl alkene in a high yield.

In the third aspect of the present invention, the alkali metal fluoride is cesium fluoride. Since a cesium ion has a large ion diameter, the solubility and nucleophilicity of fluorine ions are increased, and the generation of trialkylstannyl fluoride is carried out more rapidly. Consequently, the transmetallation from Sn to Cu is promoted, thus promoting the entire reaction.

In the fourth aspect of the present invention, the phosphine ligand is tri-o-tolylphosphine or (di-tert-butyl)methylphosphine. The present inventors have confirmed that the use of these phosphine ligands makes it possible to obtain methyl alkenes rapidly and in a higher yield. The reason therefor is thought to be because the bulkiness of tri-o-tolylphosphine and (di-tert-butyl)methylphosphine gives a highly active reaction field. Furthermore, tri-o-tolylphosphine has advantages of being a stable crystalline compound in the air and being easily handled as compared with (di-tert-butyl)methylphosphine.

In the fifth aspect of the present invention, the cuprous halide is any of cuprous bromide, cuprous chloride and cuprous iodide. When such a cuprous halide is used, a high reaction promoting effect can be achieved.

In the sixth aspect of the present invention, methyl iodide labeled with $^{11}C$, $^{12}C$, $^{13}C$, $^{14}C$ or $CD_3$ is used. When such a labeled methyl iodide is used, it can be effectively used as a tracer for kinetics study of candidate compounds for drug discovery and a tracer for a method for diagnosis of diseases by, for example, a PET method, as well as a tracer for study of the metabolism of drugs, and research and development of new pharmaceutical agents.

The method of rapid methylation of alkenes in the first to sixth aspects of the present invention can employ a two-stage synthesizing method, in which a synthesis of a methyl palladium complex and a Sn/Cu transmetallation are carried out in separate reaction vessels, and then the respective reaction solutions are mixed with each other.

That is to say, the method of rapid methylation of alkenes of the seventh aspect of the present invention includes:

a palladium complex preparation step of preparing a $CH_3PdI$ complex solution by subjecting methyl iodide, a palladium complex having a valence of 0 and a phosphine ligand in an aprotic polar solvent;

an alkenyl copper preparation step of preparing an alkenyltrialkyl copper solution by carrying out a reaction in an aprotic polar solvent in the presence of alkenyltrialkylstannane, cuprous halide, carbonate, and/or alkali metal fluoride; and a methylation step of mixing the $CH_3PdI$ complex solution and the alkenyltrialkyl copper solution so as to form methyl alkene.

In the method of rapid methylation of alkenes of the present invention, in the final stage, a complex in which a phosphine ligand is coordinated to $CH_3PdI$ and an alkenyl copper compound are subjected to a substitution reaction so as to form a complex in which a phosphine ligand is coordinated to $CH_3PdR$ (herein, R represents an alkenyl group). At this time, cuprous halide is generated as a by-product. This cuprous halide (in particular, cuprous iodide) works as a catalyst poison and inhibits the reaction. In the eighth aspect of the present invention, a synthesis of a methyl palladium complex and a Sn/Cu transmetallation are carried out in separate reaction vessels, and then the respective reaction solutions are mixed with each other. Thus, it is possible to minimize the effect as a catalyst poison of cuprous halide (in particular, cuprous iodide). Therefore, rapid methylation of alkenyltrialkylstannane can be carried out in a higher yield as compared with the case where the reaction is carried out in one reaction vessel.

It is preferable that the phosphine ligand is four times or more by a molar ratio with respect to the palladium complex having a valence of 0. According to the test results by the present inventors, when the phosphine ligand is four times or more by a molar ratio with respect to the palladium complex having a valence of 0, a high yield can be achieved.

Methyl alkene can be synthesized by preparing a kit containing a reagent used in the method of rapid methylation of alkenes of the present invention in advance, adding an aprotic polar solvent thereto, and further introducing methyl iodide thereinto. That it so say, a kit for preparing a PET tracer of the present invention includes a mixture of a palladium complex having a valence of 0, a phosphine ligand, alkenyltrialkylstannane, cuprous halide, carbonate and/or alkali metal fluoride. When such a kit for preparing a PET tracer is prepared, only by adding an aprotic polar solvent and further introducing methyl iodide, a PET tracer can be synthesized in an extremely simple manner.

Furthermore, it is preferable that a column for separating methyl alkene from a reaction solution is provided. With this configuration, it is not necessary to prepare a separation column additionally. Furthermore, a convenient kit for preparing a PET tracer can be obtained.

Furthermore, it is preferable that a first mixture containing a palladium complex having a valence of 0 and a phosphine ligand and a second mixture containing alkenyltrialkylstannane, cuprous halide, carbonate and/or alkali metal fluoride are provided separately. With this configuration, the synthesis of a methyl palladium complex and the Sc/Cu transmetallation are carried out in separate reaction vessels, and then the respective reaction solutions can be mixed with each other. Thereby, it is possible to minimize the effect as a catalyst poison of cuprous halide (in particular, cuprous iodide). Therefore, rapid methylation of alkenyltrialkylstannane can be carried out in a higher yield as compared with the case where the reaction is carried out in one reaction vessel.

Effect of the Invention

As mentioned above, when the method of the present invention is used, a Stille-coupling reaction between $SP^2$ (alkenyl) and $SP^3$ (alkyl) carbon atoms proceeds smoothly, so that methyl alkene in which a methyl group is bonded to an alkenyl group can be obtained rapidly and in a high yield.

BEST MODE OF CARRYING OUT THE INVENTION

Hereinafter, Examples of the exemplary embodiment of the present invention are described in detail in comparison with Comparative Examples. Note here that in the description below, $Pd_2(dba)_3$ represents tris(dibenzylideneacetone) dipalladium. Furthermore, $P(o\text{-tolyl})_3$ represents (tri-o-tolylphosphine), and $P(t\text{-Bu})_2Me$ represents bis(t-butyl)methylphosphine, and DMF represents N,N-dimethylformamide, respectively.

Twelve kinds of 1-alkenyltributylstannanes (4a to 4l) shown in Table 1 are selected as substrates to be used for rapid methylation. Stille-coupling reaction between $SP^2$ (alkenyl) and $SP^3$ (alkyl) carbon atoms are carried out while the molar ratio of methyl iodide and alkenyltributylstannane is set to be 1:40. The reason why too excessive alkenyltributylstannane is used is because a slight amount of $^{11}C$-labeled $CH_3I$ synthesized by cyclotron is assumed to be reacted with alkenyltributylstannane when an actual PET tracer is synthesized.

TABLE 1

| entry | 1-alkenyltributylstannane | methylated product | yield 5 [%][a,b] condition[d] | | | |
|---|---|---|---|---|---|---|
| | | | A | B | C | D |
| 1 | 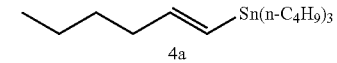<br>4a | 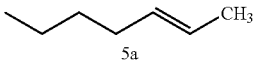<br>5a | 95 | 98 | 99 | 98 |
| 2 | 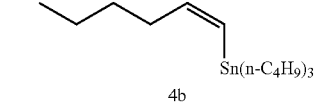<br>4b | 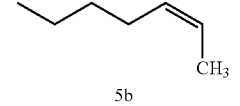<br>5b | 96 | 99 | 99 | 99 |
| 3 | 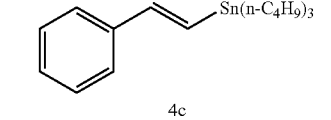<br>4c | 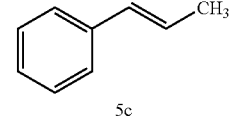<br>5c | 70 | 89<br>(88)[f] | 90 | 83<br>(87,[h] 88,[i] 91[j]) |
| 4 | 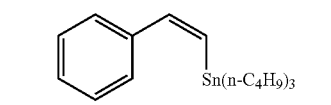<br>4d | 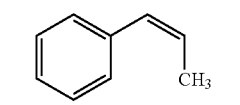<br>5d | 77 | 89<br>(89)[f] | 87<br>(90)[g] | 84<br>(90,[h] 89,[i] 95[j]) |
| 5 | 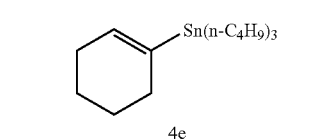<br>4e | 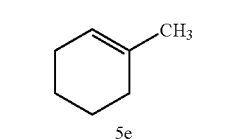<br>5e | 71 | 96 | 99 | 99 |

TABLE 1-continued

| entry | 1-alkenyltributylstannane | methylated product | yield 5 [%][a,b] condition[d] | | | |
|---|---|---|---|---|---|---|
| | | | A | B | C | D |
| 6 | HO–CH₂–C(Sn(n-C₄H₉)₃)=CH– (4f) | HO–CH₂–C(CH₃)=CH– (5fg) | 71 | 91 | 98 | 99 |
| 7 | HO–CH₂–CH=C(Sn(n-C₄H₉)₃)– (4g) | HO–CH₂–CH=C(CH₃)– (5fg) | 84 | 99 | 99 | 99 |
| 8 | (CH₃)₂C=CH–CH=C(Sn(n-C₄H₉)₃)–CH₃ (4h) | (CH₃)₂C=CH–CH=C(CH₃)–CH₃ (5h) | 77 (95)[e] | 88 (93)[f] | 95 | 89 (91)[i] |
| 9 | OHC–CH=C(Sn(n-C₄H₉)₃)–CH₃ (4i) | OHC–CH=C(CH₃)–CH₃ (5i) | 96 | 99 | 83 (80)[g] | 85 (96)[i] |
| 10 | CH₃O–C(O)–CH=CH–CH=CH–Sn(n-C₄H₉)₃ (4j) | CH₃O–C(O)–CH=CH–CH=CH–CH₃ (5j) | 94 | 95 | 99 | 86 (93)[i] |
| 11 | 3-(tributylstannyl)cyclohex-2-enone (4k) | 3-methylcyclohex-2-enone (5k) | 91 (96)[e] | 90 | 86 (90)[g] | 95 |
| 12 | methyl 6,6-dimethyl-2-(tributylstannyl)cyclohex-1-enecarboxylate (4l) | methyl 2,6,6-trimethylcyclohex-1-enecarboxylate (5l) | 71 (98)[e] | 71 (72)[f] | 54 (41)[g] | 84 (91)[i] |

As reaction conditions, the below-mentioned A to D and e to l are employed (all the ratios are shown by a molar ratio).
A: CH₃I/alkenyltributylstannane/Pd₂(dba)₃/P(o-tolyl)₃/CuCl/K₂CO₃ (1:40:0.5:2:2:2)
B: CH₃I/alkenyltributylstannane/Pd₂(dba)₃/P(o-tolyl)₃/CuCl/K₂CO₃ (1:40:0.5:4:2:5)
C: CH₃I/alkenyltributylstannane/Pd₂(dba)₃/P(t-Bu)₂Me/CuBr/CsF (1:40:0.5:2:2:2)
D: CH₃I/alkenyltributylstannane/Pd₂(dba)₃/P(o-tolyl)₃/CuBr/CsF (1:40:0.5:2:2:5)
[e] Cs₂CO₃ is used instead of K₂CO₃
[f] CH₃I/alkenyltributylstannane/Pd₂(dba)₃/P(o-tolyl)₃/CuCl/K₂CO₃ (1:40:0.5:6:2:5)
[g] CH₃I/alkenyltributylstannane/Pd₂(dba)₃/P(t-Bu)₂Me/CuCl/CsF (1:40:0.5:4:2:5)
[h] CH₃I/alkenyltributylstannane/Pd₂(dba)₃/P(o-tolyl)₃/CuCl/CsF (1:40:0.5:4:2:5)
[i] CH₃I/alkenyltributylstannane/Pd₂(dba)₃/P(o-tolyl)₃/CuBr/CsF (1:40:0.5:4:2:5)
[j] CH₃I/alkenyltributylstannane/Pd₂(dba)₃/P(o-tolyl)₃/CuI/CsF (1:40:0.5:4:2:5)
[k] CH₃I/alkenyltributylstannane/Pd₂(dba)₃/P(o-tolyl)₃/CuBr/CsF (1:40:2.5:10:10:25)
[l] CH₃I/alkenyltributylstannane/Pd₂(dba)₃/P(o-tolyl)₃/CuBr/CsF (1:40:5:20:20:50)

Note here that a to d in Table 1 have the following meanings.
[a] detected by a GLC analysis as a single product as compared with a preparation;
[b] determined by a GLC analysis based on the consumption amount of CH₃I by using n-nonane, n-heptane or n-decane as an internal standard substance (average value of twice or three times).
[c] a stereoisomer having a purity of >99:1 by the determination by 1H-NMR spectrum; and
[d] all the reactions are carried out in DMF at 60° C. for 5 minutes.

The results shown in Table 1 will be described in comparison with Comparative Examples.

(Entry 1 Condition A)

In Entry 1 Condition A, a mixture of $CH_3I/4a/Pd_2(dba)_3/P(o\text{-tolyl})_3/CuCl/K_2CO_3$ (1:40:0.5:2:2:2 by the molar ratio) in a DMF (N,N-dimethylformamide) solvent was heated at 60° C. for 5 minutes.

(Entry 2 Condition A)

Entry 2 Condition A was carried out in the same manner as in Example 1 except that a compound 4b shown in Table 1 was used as a substrate.

Comparative Example 1

Comparative Example 1 employs the conditions described by G. C. Fu et al. in non-patent documents 2 and 3. That is to say, in THF, in the presence of MS 3 Å (molecular sieve: 3 Å), $CH_3I/4a/[(\pi\text{-allyl})PdCl]_2/P(t\text{-Bu})_2Me/Me_4NF$ (1:40:0.5:3:1.9 by the molar ratio) was heated at 60° C. for 5 minutes.

Comparative Example 2

Comparative Example 2 was carried out in the same manner as in Comparative Example 1 except that a compound 4b shown in Table 1 was used as a substrate.

<Results>

In Entry 1 Condition A in which E-type isomer 4b was used as a substrate, the corresponding methylated product (E)-2-heptene (5a) was obtained as a single product in such a high yield as 95% (GLC yield based on the consumption of methyl iodide). Similarly, in Entry 2 Condition A in which Z-type isomer 4b was used as a substrate, (Z)-2-heptene (5b) was obtained in such a high yield as 96%. In this way, in Condition A, the methylation proceeds while the three-dimensional configuration is kept completely.

On the contrary, in Comparative Example 1, the yield of the intended product 5a was only 5%. Also in Comparative Example 2, it was as low as 2%.

Comparative Example 3

In Comparative Example 3, a combination of $Pd_2(dba)_3/P(t\text{-Bu})_2Me$ was used as a Pd(0)-phosphine complex and heated at 60° C. for 5 minutes in THF under the condition of $CH_3I/4a/Pd_2(dba)_3/P(t\text{-Bu})_2Me/Me_4NF$ (1:40:0.5:3:1.9 by the molar ratio).

Comparative Example 4

Comparative Example 4 was carried out in the same manner as in Comparative Example 3 except that a compound 4b shown in Table 1 was used as a substrate.

Comparative Example 5 and Comparative Example 6

Comparative Example 5 was carried out in the same manner as in Comparative Example 3 except that DMF was used as a solvent instead of the solvent in Comparative Example 3. Comparative Example 6 was carried out in the same manner as in Comparative Example 4 except that DMF was used as a solvent instead of the solvent in Comparative Example 4.

<Results>

In Comparative Example 3, the yield of the corresponding product 5a was 23%, and in Example 4, the yield of the corresponding product 5b was 7%. In both cases, the yield of obtaining the intended products was low. On the contrary, in Comparative Examples 5 and 6 in which the solvent was changed to DMF, the yields were improved to 51% and 12%, respectively. However, the yields were still low. This result shows that an aprotic polar solvent such as DMF is effective for improving the yield.

In order to confirm the generality of condition A shown in Table 1, further ten kinds of alkenyltributylstannanes 4c to 4l were subjected to cross coupling reaction with methyl iodide in the condition A. As a result, as shown in Table 1, although the yield was reduced to in the order of 70% when alkenyltrialkylstannane having a styryl structure or a substituent at a position was used as a substrate, the corresponding methyl alkene was obtained in a high yield (Entries 3 to 6, 8 and 12 in Table 1). When cesium carbonate was used instead of potassium carbonate, in substrates such as 4h, 4k and 4l having a conjugated alkene, the reaction was improved and the corresponding methyl alkene was obtained in a high yield of 95% or more (numeric references in parentheses in the condition A entries 8, 11 and 12 in Table 1). On the contrary, the yields of β-tributyl stannyl styrene or α position substituted nonconjugated alkenyl stannane were 71 to 82%. Herein, with respect to the condition A shown in Table 1, when the addition amount of $P(o\text{-tolyl})_3$ was increased to 4-6 equivalents in the presence of cuprous chloride or cuprous bromide, the yield of the reaction of 4e was significantly improved and 5e was obtained in a yield of 96 to 98%. As a result of using this condition B of $CH_3I/\text{alkenyltributylstannane}/Pd_2(dba)_3/P(o\text{-tolyl})_3/CuCl/K_2CO_3$ (1:40:0.5:4-6:2:5 by the molar ratio), as shown in Table 1, the yields of the reactions of 4c to 4h (entries 3 to 8) except for 4l were significantly improved. From this results, it was shown that using of three-dimensionally bulky triaryl phosphine and increasing of the concentration of triaryl phosphine were effective in facilitating the cross coupling.

The method described in Non-patent document 4 proposed by Baldwin et al. is applied to cross coupling between $SP^2$ and $SP^3$ carbon atoms. That is to say, heating was carried out at 60° C. for 5 minutes in DMF under the conditions of $CH_3I/\text{alkenyltributylstannane}/Pd[(PPh)_3]_4/CuI/CsF$ (1:40:1:4:2:2 by the molar ratio) and $CH_3I/\text{alkenyltributylstannane}/PdCl_2/P(t\text{-Bu})_3\ CuI/CsF$ (1:40:1:2:2:2 by the molar ratio). As a result, 4e and 5e shown in Table 1 were obtained in a yield of 24% and 2%, respectively.

Similarly, $Pd_2/(dba)_3$/phosphine was used as Pd(0)-phosphine complex and heating was carried out at 60° C. for 5 minutes in DMF under the conditions of $CH_3I/\text{alkenyltributylstannane}/Pd_2(dba)_3/PPh_3/CuI/CsF$ (1:40:0.5:4:2:5 by the molar ratio) and $CH_3I/\text{stannane}/Pd_2(dba)_3/P(t\text{-Bu})_3/CuI/CsF$ (1:40:0.5:2:2:2 by the molar ratio). As a result, 4e and 5e were obtained in a yield of 31% and 27%, respectively.

<Reaction Promoting Effect when Bulky Phosphine Ligand is Used>

A series of Examples when $P(t\text{-Bu})_2Me$ and $P(o\text{-tolyl})_3$ that are bulky phosphine ligands are used are shown in Tables 2A and 2B.

TABLE 2

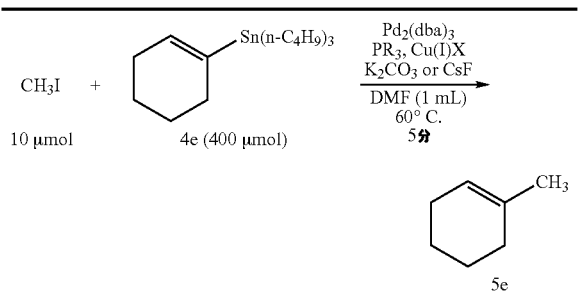

Table 2A

| | | column | | | | | | | | |
|---|---|---|---|---|---|---|---|---|---|---|
| | | 1 | 2 | 3 | 4 | 5 | 6 | 7 | 8 | 9 |
| | | | | | | additive | | | | |
| | | CuCl (2) | | | CuBr (2) | | | CuI (2) | | |
| | equi- | $K_2CO_3$ | | | $K_2CO_3$ | | | $K_2CO_3$ | | |
| entry | phosphine | valent) | (0) | (2) | (5) | (0) | (2) | (5) | (0) | (2) | (5) |
| 1 | P(o-tolyl)$_3$ | (2) | — | 71 | 84 | — | 56 | 82 | — | 21 | 51 |
| 2 | | (4) | — | 76 | 96 | — | 59 | 96 | — | 23 | 50 |
| 3 | | (6) | — | 79 | 98 | — | 61 | 98 | — | 27 | 63 |

Table 2B

| | | column | | | | | | | | |
|---|---|---|---|---|---|---|---|---|---|---|
| | | 1 | 2 | 3 | 4 | 5 | 6 | 7 | 8 | 9 |
| | | | | | | additive | | | | |
| | | CuCl (2) | | | CuBr (2) | | | CuI (2) | | |
| | equi- | CsF | | | CsF | | | CsF | | |
| entry | phosphine | valent) | (0) | (2) | (5) | (0) | (2) | (5) | (0) | (2) | (5) |
| 1 | P(t-Bu)$_2$Me | (2) | — | 43 | 99 | 40 | 99 | 99 | — | 27 | 99 |
| 2 | | (4) | — | — | 99 | — | 36 | 33 | — | — | 99 |
| 3 | P(o-tolyl)$_3$ | (2) | — | — | 96 | 31 | 66 | 99 | — | — | 38 |
| 4 | | (4) | 47 | 86 | 99 | — | — | 99 | 18 | 59 | 99 | a: the yield of 5e was determined by a GLC analysis based on the consumption amount of CH3I by using n-nonane as an internal standard substance. (-: no data). An average value of two values. Reaction condition: CH3I/4e/Pd2(dba)3/PR3/CuX (X = Cl, Br, or I)/K2CO3 or CsF (1:40:0.5:2, 4, or 6:2:0, 2 or 5 by the molar ratio). In DMF. At 60° C. for 5 minutes. Numeric references in parentheses represent the equivalents with respect to methyl iodide.

(Description of References in Table)
a: the yield of 5e was determined by a GLC analysis based on the consumption amount of CH$_3$I by using n-nonane as an internal standard substance. (-: no data). An average value of two values.

Reaction condition: CH$_3$I/4e/Pd$_2$(dba)$_3$/PR$_3$/CuX (X═Cl, Br, or I)/K$_2$CO$_3$ or CsF (1:40:0.5:2, 4, or 6:2:0, 2 or 5 by the molar ratio). In DMF. At 60° C. for 5 minutes. Numeric references in parentheses represent the equivalents with respect to methyl iodide.

Table 2 shows that when a bulky phosphine ligand such as P(t-Bu)$_2$Me and P(o-tolyl)$_3$ are used, the reaction is significantly promoted and high yield can be achieved. For example, when P(t-Bu)$_2$Me/CuCl or CuI/CsF (2 or 4:2:5 by the molar ratio) is used, a coupling product can be obtained in a yield of 99% (Entries 1 and 2, columns 3 and 9 in Table 2B; modified conditions C in Table 1). Furthermore, it is shown that the more the addition amount of potassium carbonate or cesium fluoride is, the higher the yield becomes. It is also shown that when the addition amount of the phosphine ligand is increased, the yield becomes higher. For example, under the condition in which P(o-tolyl)$_3$ (2 equivalents), CuBr (2 equivalents) and CsF (5 equivalents) were used, 5e was obtained in a yield of 99% (Entry 3, column 6 in Table 2B; condition D in Table 1). Furthermore, when the addition amount of this three-dimensionally bulky phosphine was increased (4 equivalents), the reaction proceeded almost perfectly (Entry 4, columns 3, 6 and 9 in Table 2B; modified condition D in Table 1).

The reaction was carried out under the condition in which the conditions C and D in Table 1 were somewhat modified. That is to say, CH$_3$I/alkenyltributylstannane/Pd$_2$(dba)$_3$/P(t-Bu)$_2$Me/CuX/CsF (1:40:0.5:2-4:2:2-5 by the molar ratio) and CH$_3$I/alkenyltributylstannane/Pd$_2$(dba)$_3$/P(o-tolyl)$_3$/CuX/CsF (1:40:0.5:2-4:2:5 by the molar ratio) were applied to all the other tin compounds 4a to 4d and 4f to 4l. As a result, in the condition D and the modified condition D based on the addition amount of P(o-tolyl)$_3$, with all substrates, a coupling product was obtained in a yield of 90% or more. However, in the condition C, in Entries 9 and 12, the reaction promoting effect was much less effective than that in the condition D. The difference is estimated to be because trialkyl phosphine has higher nucleophilicity and tends to cause 1,4-addition reaction to α, β-unsaturated carbonyl group as compared with triaryl phosphine.

In the case of P(o-tolyl)$_3$, when a large amount of phosphine ligand was used, an excellent result was obtained (modified condition D, Entries 9 and 12 in Table 1). Furthermore, since P(t-Bu)$_2$Me is in an oily state and is an unstable compound in the air, it needs to be handled in a glove box in an atmosphere of inactive gas. On the contrary, P(o-tolyl)$_3$ is a stable crystalline compound in the air, so that handling is easy.

Furthermore, as shown in Table 2B, it has been found that the use of Cu(I)X, CsF and a phosphine ligand in combination is extremely effective for coupling reaction. The high reaction promoting effect by using the combination of cuprous halide and CsF is described by a synergistic effect of the production of the highly reactive active organocopper by a Sn/Cu transmetallation, and the equilibrium shift to alkenyl copper by the removal to the outside of (n-Bu)$_3$SnX by the production of insoluble (n-Bu)$_3$SnF.

The amount of $^{11}$C-labeled CH$_3$I to be used in the actual synthesis of PET tracers is very small. Therefore, in the amount of reagent to be used for CH$_3$I, Pd/CuX/alkali metal fluoride is also necessarily excessive in addition to alkenyltrialkylstannane as a scavenger. From this viewpoint, when the reaction was carried out under the conditions of CH$_3$I/4e/Pd$_2$(dba)$_3$/P(o-tolyl)$_3$/CuBr/CsF (1:40:2.5:10:10:25 by the molar ratio) and (1:40:5:20:20:5 by the molar ratio) in which Pd/CuX/alkali metal fluoride was increased by 5 times and 10 times as CH$_3$I, 5e was obtained in a yield of 99%, respectively (Entry 5 in Table 1). In this way, it was shown that the yield was not much reduced even if the equivalent ratio of the catalyst system is increased with respect to methyl iodide.

As shown in the experiment results mentioned above, the inventors of the present application have established a rapid methylation method that is a base technology for introducing a $^{11}$C-labeled methyl group into alkenes (see Chemical Formula 1).

[Chemical Formula 1]

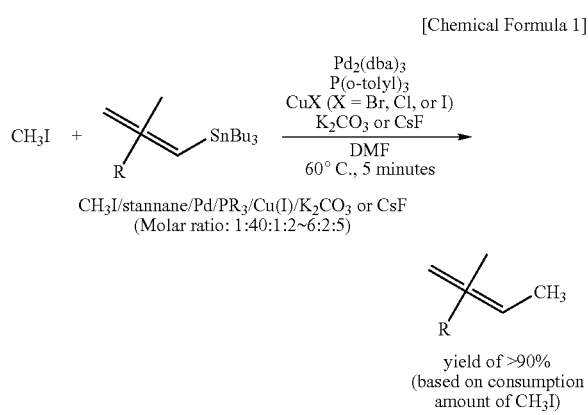

CH₃I/stannane/Pd/PR₃/Cu(I)/K₂CO₃ or CsF
(Molar ratio: 1:40:1:2~6:2:5)

yield of >90%
(based on consumption amount of CH₃I)

Furthermore, the inventors of the present application have investigated a two-stage synthesizing method of methyl alkene. That is to say, methyl iodide, a palladium complex having a valence of 0 and a phosphine ligand are reacted with each other in an aprotic polar solvent to form a CH₃PdI complex solution. Furthermore, the reaction is carried out in the presence of alkenyltrialkylstannane, cuprous halide, carbonate and/or alkali metal fluoride, in an aprotic polar solvent so as to form an alkenyltrialkyl copper solution. Then, a CH₃PdI complex solution and an alkenyltrialkyl copper solution are mixed with each other to form methyl alkene. More specifically, firstly, based on the condition of CH₃I/4e/Pd₂(dba)₃/P(o-tolyl)₃/CuBr/CsF (1:40:2.5:10:10:25 by the molar ratio) using five times larger amount of Pd/Cu/F additive agent with respect to methyl iodide, in DMF, methyl iodide was reacted with a Pd(o-tolyl)₃ complex produced by mixing Pd₂(dba)₃ and P(o-tolyl)₃ (1:4) by stirring thereof at room temperature for one minute. Then, this solution was transferred to a DMF mixture solution of 4e/CuBr/CsF and the mixture solution was heated at 60° C. for 5 minutes. As a result, the intended 5e was obtained in a yield of 99% (modified condition D, Entry 5 in Table 1). Even when a staged operation method based on the condition D was carried out, the yield was not deteriorated. It was shown that the staged operation method was sufficiently applicable. This condition was used for introduction of ¹¹C mentioned below.

Next, based on this result, an actual synthesis of a PET tracer was carried out. That is to say, ¹¹C-labeled CH₃I was captured by using 4l as alkenyltrialkylstannane. Under the conditions B and D (more effective staged operation method was applied), the intended 5l labeled with ¹¹C was obtained in a high radiochemical yield (HPLC analysis yield) of 85% in both conditions. From the results, it can be easily estimated that ¹¹C methylation of other alkenyltrialkylstannanes can proceed in a high yield under such conditions.

[Chemical Formula 2]

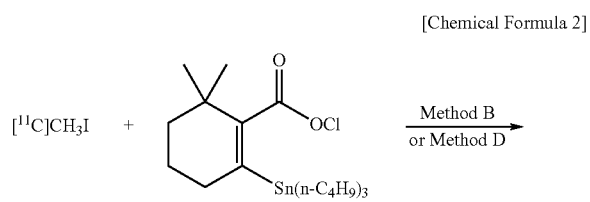

-continued

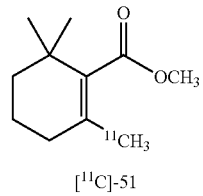

[¹¹C]-5l radiochemical yield (HPLC analysis yield) Method B: 85%; Method D: 85%

The ¹¹C-labeled methyl iodide to be used in the present invention can be obtained by using a synthesizer (manufactured by GE) for synthesizing ¹¹C-labeled methyl iodide by a vapor phase reaction of CH₄ and I2 which are labeled with ¹¹C or by a method described by Ferrieri and Wolf et al. (R. A. Ferrieri and P. Wolf, Radiochem. Acta, 1983, 34, 69-83).

For the synthesis of the labeled methyl iodide used in this present invention, not only ¹¹C, but also labeled compound such as ¹²C, ¹³C, ¹⁴C and CD₃ can be used.

Hereinafter, Examples showing the method of rapid methylation of alkenes of the present invention are described in more detail.

Example 1

(Experiment Example of Substrate of Entry 1 in Table 1 Under Condition A)

Tris(dibenzylideneacetone) dipalladium (0) (4.6 mg, 5.0 μmol), tri-o-triphosphine (6.1 mg, 20 μmol), copper chloride (2.0 mg, 20 μmol) and potassium carbonate (2.8 mg, 20 tμmol) were placed in a 10-ml dry Schlenk flask under argon atmosphere, and an N,N-dimethylformamide (DMF) solvent (0.5 ml) was added thereto. Then, the mixture was heated at room temperature for 5 minutes. Then, a DMF (0.5 ml) solution of tin compound 4a (149 mg, 400 μmol) and a DMF solution of methyl iodide (12.5 μl, 0.80M, 10 μmol) were added to the mixture, sequentially. The mixture was heated at 60° C. for 5 minutes. Then, the reaction solution was quickly cooled in an ice bath. Diethyl ether (1 ml) was added and the mixture was then loaded on a short column of silica gel (0.5 g) and eluted with diethyl ether (1 ml). Then, 5.0 mol of DMF solution of n-nonane (50 μl, 0.10M (1M=1 mol/l (litter)) as an internal standard substance was added to the eluate, and the mixture was subjected to a GLC analysis (GCMS-QP5050A (Shimadzu) equipped with a mass spectrometer; capillary column: GL Science TC-5, 60×0.25 mm i.d., df=0.25 μm; carrier gas: He; flow rate: 0.8 ml/min; temperature of a sample introducing part: 280° C.; temperature of a detector: 280° C.; temperature of a column: initial temperature 80° C., final temperature 100° C.; temperature increase rate: 5° C./min, 10-14 minutes). As a result, (E)-2-heptene (5a) was obtained in a yield of 95% based on methyl iodide. Retention time: 6.1 minutes (n-nonane: 8.8 minutes).

Example 2

(Experiment Example of Substrate of Entry 9 in Table 1 Under Condition B)

Tris(dibenzylideneacetone) dipalladium (0) (4.6 mg, 5.0 μmol), tri-o-triphosphine (12.2 mg, 40 μmol), copper chloride (2.0 mg, 20 μmol) and potassium carbonate (6.9 mg, 50 μmol) were placed in a 10-ml dry Schlenk flask under argon atmosphere, and an N,N-dimethylformamide (DMF) solvent (0.5 ml) was added thereto. Then, the mixture was heated at room temperature for 5 minutes. Then, a DMF (0.5 ml) solution of tin compound 4i (143 mg, 400 µmol) and a DMF solution of methyl iodide (12.5 µl, 0.80M, 10 µmol) were added to the mixture, sequentially. The mixture was heated at 60° C. for 5 minutes, and then the reaction solution was quickly cooled in an ice bath. Diethyl ether (1 ml) was added thereto. Then, the mixture was loaded on a short column of silica gel (0.5 g) and eluted with diethyl ether (1 ml). Then, n-nonane (50 µl, 0.10M DMF solution, 5.0 µmol) as an internal standard substance was added to the eluate and the mixture was subjected to a GLC analysis (GC-2010 (Shimadzu) equipped with a flame ionization detector; capillary column: GL Science TC-1701, 60×0.25 mm i.d., df=0.25 µm; carrier gas: He; flow rate: 0.4 ml/min; temperature of a sample introducing part: 280° C.; temperature of a detector: 280° C.; temperature of a column: initial temperature 80° C., final temperature 100° C.; temperature increase rate: 5° C./min, 10-14 minutes). As a result, 3-methyl-2-butenal (5l) was obtained in a yield of 99% based on methyl iodide. Retention time: 10.5 minutes (n-nonane: 10.3 minutes).

Example 3

(Experiment Example of Substrate of Entry 7 in Table 1 Under Condition C)

Tris(dibenzylideneacetone) dipalladium (0) (4.6 mg, 50 µmol), di-t-butyl methylphosphine (3.2 mg, 20 µmol), copper bromide (2.9 mg, 20 µmol) and cesium fluoride (7.6 mg, 50 µmol) were placed in a 10-ml dry Schlenk flask under argon atmosphere, and an N,N-dimethylformamide (DMF) solvent (0.5 ml) was added thereto. Then, the mixture was stirred at room temperature for 5 minutes. Then, a DMF (0.5 ml) solution of tin compound 4g (144 mg, 400 µmol) and a DMF solution of methyl iodide (12.5 µl, 0.80M, 10 µmol) were added to the mixture, sequentially. The mixture was heated at 60° C. for 5 minutes. Then, the reaction solution was quickly cooled in an ice bath. Diethyl ether (1 ml) was added, and the mixture was then loaded on a short column of silica gel (0.5 g) and eluted with diethyl ether (1 ml). Then, n-decane (50 µl, 0.10M DMF solution, 5.0 µmol) as an internal standard substance was added to the eluate, and the mixture was subjected to a GLC analysis (GC-2010 (Shimadzu) equipped with a flame ionization detector; capillary column: GL Science TC-WAX, 60×0.25 mm i.d., df=0.25 µm; carrier gas: He; flow rate: 0.4 ml/min; temperature of a sample introducing part: 280° C.; temperature of a detector: 280° C.; temperature of a column: initial temperature 150° C., final temperature 200° C.; temperature increase rate: 10° C./min, 10-15 minutes). As a result, 3-methyl-2-buten-1-ol (5 fg) was obtained in a yield of 99% based on methyl iodide. Retention time: 9.6 minutes (n-nonane: 8.5 minutes).

Example 4

(Experiment Example of Substrate of Entry 5 Under Condition D in Table 1)

Tris(dibenzylideneacetone) dipalladium (0) (4.6 mg, 5.0 µmol), tri-o-tolylphosphine (6.1 mg, 20 µmol), copper bromide (2.9 mg, 20 µmol) and cesium fluoride (7.6 mg, 50 µmol) were placed in a 10-ml dry Schlenk flask under argon atmosphere, and an N,N-dimethylformamide (DMF) solvent (0.5 ml) was added thereto. Then, the mixture was stirred at room temperature for 5 minutes. Then, a DMF (0.5 ml) solution of tin compound 4e (148 mg, 400 µmol) and a DMF solution of methyl iodide (12.5 µl, 0.80M, 10 µmol) were added to the mixture, sequentially. The mixture was heated at 60° C. for 5 minutes. The reaction solution was quickly cooled in an ice bath. Diethyl ether (1 ml) was added and the mixture was then loaded on a short column of silica gel (0.5 g) and eluted with diethyl ether (1 ml). Then, n-nonane (50 µl, 0.10M DMF solution, 5.0 µmol) as an internal standard substance was added to the eluate and the mixture was subjected to a GLC analysis (GC-2010 (Shimadzu) equipped with a flame ionization detector; capillary column: GL Science TC-1701, 60×0.25 mm i.d., df=0.25 µm; carrier gas: He; flow rate: 0.4 ml/min; temperature of a sample introducing part: 280° C.; temperature of a detector: 280° C.; temperature of a column: initial temperature 80° C., final temperature 100° C.; temperature increase rate: 5° C./min, 10-14 minutes). As a result, 1-methylcyclohexanone (5e) was obtained in a yield of 99% based on methyl iodide. Retention time: 13.1 minutes (n-nonane: 17.2 minutes).

Example 5

A DMF (270 µl) solution of tris(dibenzylideneacetone) dipalladium (1.8 mg, 1.97 µmol) and tris-o-triphosphine (2.4 mg, 7.9 µmol) was prepared in a 0.5-ml reaction vessel A and set at room temperature. Meanwhile, a DMF (60 µl) solution of tin compound 4l (2.1 mg, 4.5 µmol), copper chloride (2.0 mg, 20 µmol), and potassium carbonate (2.8 mg, 20 µmol) was prepared in a 1.0-ml reaction vessel B and set at room temperature. Next, [$^{11}$C] methyl iodide was captured in the reaction vessel A at room temperature and stood still for one minute. This solution was transferred to the reaction vessel B. Then, the inside of the reaction vessel A was washed with 40 µl of DMF and this washed solution was also transferred to the reaction vessel B. The obtained mixture solution was heated at 65° C. for 5 minutes. Then, the reaction solution was filtered through a cotton plug (or filtered through an SPE solid phase extraction column) by using a DMF:H$_2$O (1:5) solution (300 µl). The filtrate was subjected to HPLC and the intended [$^{11}$C] methylated product was separated and purified. [$^{11}$C] methylated product, which had been aliquoted from [$^{11}$C]-51 in a radiochemical yield of 85%, was concentrated in an evaporator so as to form a specified solution for clinical administration.

Example 6

A DMF (270 µl) solution of tris(dibenzylideneacetone) dipalladium (1.8 mg, 1.97 µmol) and tri-o-triphosphine (2.4 mg, 7.9 µmol) was prepared in a 0.5-ml reaction vessel A and set at room temperature. Meanwhile, a DMF (60 µl) solution of tin compound 4l (2.1 mg, 4.5 µmol), copper bromide (2.9 mg, 20 µmol), and cesium fluoride (7.6 mg, 50 µmol) was prepared in a 1.0-ml reaction vessel B and set at room temperature. Next, [$^{11}$C] methyl iodide was captured in the reaction vessel A at room temperature and stood still for one minute. This solution was transferred to the reaction vessel B. Then, the inside of the reaction vessel A was washed with 40 µl of DMF and this washed solution was also transferred to the reaction vessel B. The obtained mixture solution was heated at 65° C. for 5 minutes. Then, the reaction solution was filtered through a cotton plug (or filtered through an SPE solid phase extraction column) by using a DMF:H$_2$O (1:5) solution (300 µl). The filtrate was subjected to HPLC and the intended [$^{11}$C] methylated product was separated and purified. [$^{11}$C] methylated product, which had been aliquoted from [$^{11}$C]-51 in a radiochemical yield of 85%, was concentrated in an evaporator so as to form a specified solution for clinical administration. Note here that it is thought that this reaction can be synthesized by a one-pot operation. However, in this Example, a two-pot operation that is more effective for synthesizing a PET tracer was employed.

The above-mentioned methylated product labeled with $^{11}C$ (hereinafter, referred to as "[$^{11}C$] methylated product") can be synthesized by using a general PET tracer synthesizer, for example, a solution transferring type synthesizer, a robot-arm type synthesizer, or the like. Furthermore, a kit for synthesizing a PET tracer for the purpose of synthesizing the above-mentioned [$^{11}C$] methylated product can be produced. This synthesizing kit is used to synthesize the intended [$^{11}C$] methylated product by setting the necessary amount of reactant, tin compound and DMF solvent in each reaction vessel in advance and by transferring the solution by a septum-cannulation method by a remote control operation.

Hereinafter, based on the above-mentioned Examples, Examples assumed to be highly feasible (kit and solution for clinical administration) will be mentioned. These Examples have not been carried out, however, they could be carried out with high probability if they are carried out based on the high level findings of the present inventors. Therefore, clear numeric values are given. Note here that Examples 7 and 8 relate to a kit for preparing a PET tracer; Examples 9 and 10 relate to a solution for clinical administration employing the One Pot operation method; and Examples 11 and 12 relate to a solution for clinical administration employing the Two Pot operation method.

Example 7

1.8 mg (1.97 μmol) of tris(dibenzylideneacetone) dipalladium (0), 2.4 mg (7.88 μmol) of tri-o-tolylphosphine, 2.0 mg (20 μmol) of copper chloride, 2.8 mg (20 μmol) of potassium carbonate and 1.6 mg (4.5 μmol) of tin compound 4a are measured and placed in a micro-tube. A cotton plug filter and a solid phase extraction column are used as one set. Thus, it is possible to produce a kit for preparing a PET tracer of the compound shown in Example 1 containing a [$^{11}C$] methyl group by methylation reaction.

A PET tracer containing a [$^{11}C$] methyl group by a methylation reaction is prepared as follows. A reagent of the above-mentioned kit is dissolved in the attached N,N-dimethylformamide (DMF) solvent (1.0 ml); an additionally prepared [$^{11}C$] methyl iodide is added to be mixed, and reacted at 60° C. for 5 minutes; and the reaction solution is cooled and then poured through the attached solid phase extraction column. Then, the filtrate is subjected to HPLC so as to separate and purify the intended [$^{11}C$] methyl labeled compound.

Example 8

1.8 mg (1.97 μmol) of tris(dibenzylideneacetone) dipalladium (0), 1.3 mg (8.11 μmol) of di-t-butyl methylphosphine, 2.9 mg (20 μmol) of copper bromide, 7.6 mg (50 μmol) of cesium fluoride and 1.6 mg (4.5 μmol) of tin compound 4g are measured and placed in a micro-tube. A cotton plug filter and a solid phase extraction column are used as one set. Thus, it is possible to produce a kit for preparing a PET tracer of the compound shown in Example 4 containing a [$^{11}C$] methyl group by a methylation reaction.

A PET tracer containing a [$^{11}C$] methyl group by a methylation reaction is prepared as follows. A reagent of the above-mentioned kit is dissolved in the attached N,N-dimethylformamide (DMF) solvent (1.0 ml); an additionally prepared [$^{11}C$] methyl iodide is added to be mixed, and reacted at 60° C. for 5 minutes; and the reaction solution is cooled and then poured through the attached solid phase extraction column. Then, the filtrate is subjected to HPLC so as to separate and purify the intended [$^{11}C$] methyl labeled compound.

Example 9

A DMF (0.4 ml) solution of a tin compound 4l (2.1 mg, 4.5 μmol), tris(dibenzylideneacetone) dipalladium (1.8 mg, 1.97 μmol), tri-o-tolylphosphine (2.4 mg, 7.9 μmol), copper chloride (2.0 mg, 20 μmol), and potassium carbonate (2.8 mg, 20 μmol) was prepared in a 1.0-ml reaction vessel and set at room temperature. Then, [$^{11}C$] methyl iodide was captured in this solution at room temperature and stood still for one minute. The obtained mixture solution was heated at 65° C. for 5 minutes. Then, the reaction solution was filtered through a cotton plug (or filtered through an SPE solid phase extraction column) by using a DMF:$H_2O$ (1:5) solution (300 μl). The filtrate was subjected to HPLC. The intended [$^{11}C$] methylated product was concentrated in an evaporator so as to form a specified solution for clinical administration.

Example 10

A DMF (0.4 ml) solution of a tin compound 4l (2.1 mg, 4.5 μmol), tris(dibenzylideneacetone) dipalladium (1.8 mg, 1.97 μmol), tri-o-tolylphosphine (2.4 mg, 7.9 μmol), copper bromide (2.9 mg, 20 μmol) and cesium fluoride (7.6 mg, 50 μmol) was prepared in a 1.0-ml reaction vessel and set at room temperature. Then, [$^{11}C$] methyl iodide was captured in this solution at room temperature and stood still for one minute. The obtained mixture solution was heated at 65° C. for 5 minutes. Then, the reaction solution was filtered through a cotton plug (or filtered through an SPE solid phase extraction column) by using a DMF:$H_2O$ (1:5) solution (300 μl). The filtrate was subjected to HPLC and the intended [$^{11}C$] methylated product was separated and purified. The aliquoted [$^{11}C$] methylated product was concentrated in an evaporator so as to form a specified solution for clinical administration.

Example 11

Tris(dibenzylideneacetone) dipalladium (0) (1.8 mg, 1.97 μmol) and tri-o-tolylphosphine (2.4 mg, 7.9 μmol) were measured and placed in a 0.5-ml reaction vessel A. The reaction mixture was dissolved in a DMF solution (270 μl) and set at room temperature. Meanwhile, tin compound 4l (2.1 mg, 4.5 μmol), copper chloride (2.0 mg, 20 μmol) and potassium carbonate (2.8 mg, 20 μmol) were measured and placed in a 1.0-ml reaction vessel B. The reaction mixture was dissolved in a DMF (60 μl) and set at room temperature. Next, [$^{11}C$] methyl iodide was captured in the reaction vessel A at room temperature and stood still for one minute. This solution was transferred to the reaction vessel B by a septum-cannulation method. Then, the inside of the reaction vessel A was washed with 40 μl of DMF and this solution was also transferred to the reaction vessel B. The obtained mixture solution was heated at 65° C. for 5 minutes. Then, the reaction solution was filtered through a cotton plug (or filtered through an SPE solid phase extraction column) by using a DMF:$H_2O$ (1:5) solution (300 μl). The filtrate was subjected to HPLC and the intended [$^{11}C$] methylated product was separated and purified. The aliquoted [$^{11}C$] methylated product was concentrated in an evaporator so as to form a specified solution for clinical administration.

Example 12

Tris(dibenzylideneacetone) dipalladium (0) (1.8 mg, 1.97 μmol) and tri-o-tolylphosphine (2.4 mg, 7.9 μmol) were measured and placed in a 0.5-ml reaction vessel A. The reaction mixture was dissolved in a DMF (270 μl) and set at room temperature. Meanwhile, tin compound 4l (2.1 mg, 4.5 μmol), copper bromide (2.9 mg, 20 μmol) and cesium fluoride (7.6 mg, 50 μmol) were measured and placed in a 1.0-ml reaction vessel B. The reaction mixture was dissolved in a DMF (60 μl) and set at room temperature. Next, [$^{11}$C] methyl iodide was captured in the reaction vessel A at room temperature and stood still for one minute. This solution was transferred to the reaction vessel B by a septum-cannulation method. Then, the inside of the reaction vessel A was washed with 40 μl of DMF and this solution was also transferred to the reaction vessel B. The obtained mixture solution was heated at 65° C. for 5 minutes. Then, the reaction solution was filtered through a cotton plug (or filtered through an SPE solid phase extraction column) by using a DMF:H$_2$O (1:5) solution (300 μl). The filtrate was subjected to HPLC and the intended [$^{11}$C] methylated product was separated and purified. The aliquoted [$^{11}$C] methylated product was concentrated in an evaporator so as to form a specified solution for clinical administration.

As mentioned above, the present invention is described based on Examples. However, the present invention is not limited to the description of the above Examples. A variety of modifications can be made as long as they are within the scope of the contents of the present invention. Such modifications are also encompassed in the present invention.

INDUSTRIAL APPLICABILITY

The invention of the present application can be used as a method for manufacturing a PET tracer in medical industry, and the like.

The invention claimed is:

1. A method of rapid methylation of alkenes, the method comprising;
    subjecting methyl iodide and alkenyltrialkylstannane to cross coupling in an aprotic polar solvent in a presence of a palladium complex having a valence of 0, said complex being tris(dibenzylideneacetone) dipalladium (0), a phosphine ligand being tri-o-tolylphosphine or (di-tert-butyl)methylphosphine, cuprous halide, and a carbonate or alkali metal fluoride.

2. The method of rapid methylation of alkenes according to claim 1, wherein the carbonate is potassium carbonate or cesium carbonate.

3. The method of rapid methylation of alkenes according to claim 1, wherein the alkali metal fluoride is cesium fluoride.

4. The method of rapid methylation of alkenes according to claim 1, wherein the cuprous halide is any of cuprous bromide, cuprous chloride and cuprous iodide.

5. The method of rapid methylation of alkenes according to claim 1, wherein methyl iodide labeled with $^{11}$C, $^{12}$C, $^{13}$C, $^{14}$C or CD$_3$ is used.

6. The method of rapid methylation of alkenes according to claim 1, the method comprising:
    a palladium complex preparation step of preparing a CH$_3$PdI complex solution by reacting methyl iodide, a palladium complex having a valence of 0, said complex being tris(dibenzylideneacetone) dipalladium (0), and a phosphine ligand being tri-o-tolylphosphine or (di-tert-butyl)methylphosphine with each other in an aprotic polar solvent;
    an alkenyl copper preparation step of preparing an alkenylcopper solution by carrying out a reaction in an aprotic polar solvent in a presence of alkenyltrialkylstannane, cuprous halide, carbonate, and/or alkali metal fluoride; and
    a methylation step of mixing the CH$_3$PdI complex solution and the alkenyltrialkyl copper solution so as to form methyl alkene.

7. The method of rapid methylation of alkenes according to claim 1, wherein the phosphine ligand is four times or more by a molar ratio with respect to the palladium complex having a valence of 0.

8. The method of rapid methylation of alkenes according to claim 1, wherein the alkali metal fluoride is cesium fluoride.

* * * * *